(12) United States Patent
Tran et al.

(10) Patent No.: US 6,310,244 B1
(45) Date of Patent: *Oct. 30, 2001

(54) PHOTOCLEAVABLE AND ACID CLEAVABLE LINKERS FOR COMBINATORIAL CHEMISTRY

(75) Inventors: Vinh D. Tran, East Windsor; Vu Van Ma, Plainsboro; Ruiyan Liu, North Brunswick, all of NJ (US)

(73) Assignee: Pharmacopeia, Inc., Princeton, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/121,262

(22) Filed: Jul. 23, 1998

(51) Int. Cl.[7] ............... C07C 233/04; C07C 233/16; C07C 233/29; C07C 235/18
(52) U.S. Cl. ............... 564/155; 204/157.81; 564/166; 564/169
(58) Field of Search .................. 564/155, 166, 564/169; 204/157, 81

(56) References Cited

U.S. PATENT DOCUMENTS 5,739,386  4/1998  Holmes ................ 562/437

OTHER PUBLICATIONS

Ming Lee, S. et al. "Photo–Cross–Linking of Poly(4–hydroxystyrene) via Electrophilic Aromatic Substitution: Use of Polyfunctional Benzylic Alcohols in the Design of Chemically Amplified . . . ", Macromolecules, vol. 27, No. 18, pp 5154–5159 (1994).

Seneci, Pierfausto et al. "Combinatorial Chemistry and Natural Prods. Teicoplanin Aglycone as a Molecular Scaff. for Solid Phase Synthesis of Comb. Libraries." Tetrahedron Letters, vol. 37, No. 35, pp6319–6322 (1996).

Primary Examiner—Floyd D. Higel
(74) Attorney, Agent, or Firm—Heslin Rothenberg Farley & Mesiti P.C.

(57) ABSTRACT

A substrate for solid phase synthesis comprising a solid phase-linker combination of the formula I is disclosed. Also disclosed are processes for preparing the substrate and chemical intermediates useful therein. Among the novel intermediates are compounds of the formula II wherein $R^1$ is —$NO_2$ or —CHO; $R^2$ is —$OCH_3$, —CHO or —H; $R^3$ is chosen from the group consisting of hydroxyl, the residue of a solid support having a plurality of amino groups, and the residue of an ester, and n=1 or 3.

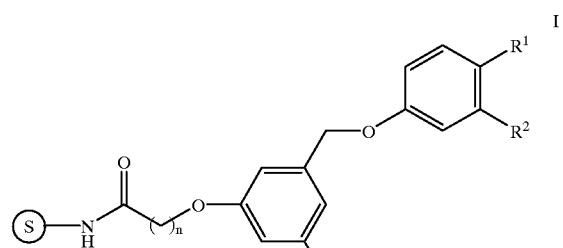

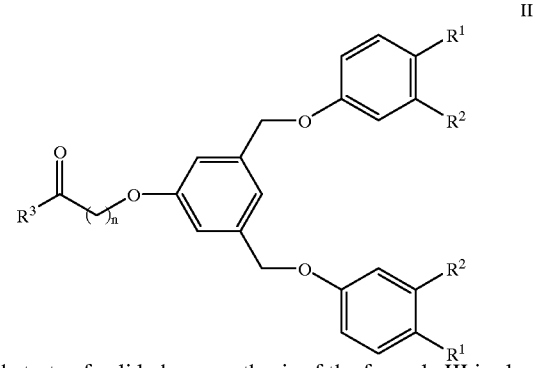

A substrate of solid phase synthesis of the formula III is also disclosed.

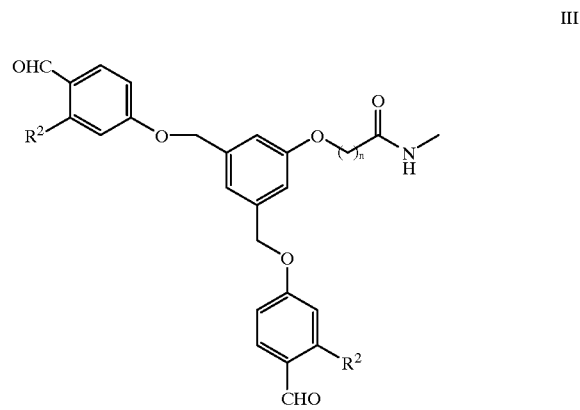

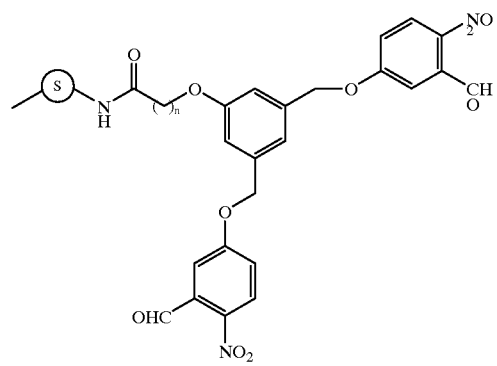

5 Claims, No Drawings

PHOTOCLEAVABLE AND ACID CLEAVABLE LINKERS FOR COMBINATORIAL CHEMISTRY

FIELD OF THE INVENTION

This invention relates generally to the synthesis of chemical compounds, and more particularly, to the solid phase synthesis of combinatorial libraries of chemical compounds.

BACKGROUND OF THE INVENTION

Combinatorial organic synthesis is becoming an important tool in drug discovery. Methods for the synthesis of large numbers of diverse compounds have been described (Ellman et al., *Chem. Rev.* 96, 555–600 (1996)), as have methods for tagging systems (Ohlmeyer et al., *Proc. Natl. Acad. Sci. USA* 90, 10922–10926 (1993)). The growing importance of combinatorial synthesis has created a need for new resins and linkers having chemical and physical properties that accommodate a wide range of conditions. Success in combinatorial synthesis on solid phase supports depends on the ability to synthesize diverse sets of molecules and to then cleave those molecules from the supports cleanly and in good yield.

Linkers are molecules that are attached to a solid support and to which the desired members of a library of chemical compounds may in turn be attached. When the construction of the library is complete, the linker allows clean separation of the target compounds from the solid support without harm to the compounds and preferably without damage to the support. Several linkers have been described in the literature. Their value is constrained by the need to have sufficient stability which allows the steps of combinatorial synthesis under conditions that will not cleave the linker. An additional constraint is the need to have a fairly high lability under at least one set of conditions that is not employed in the chemical synthesis.

For example, if an acid labile linker is employed, then the combinatorial synthesis must be restricted to reactions that do not require the presence of an acid of sufficient strength to endanger the integrity of the linker. Likewise, when a photocleavable linker is employed, conditions that exclude light are necessary to avoid untimely cleavage of the compound from the resin. This sort of balancing act often imposes serious constraints on the reactions that are chosen for preparation of the library.

The 4-[4-(hydroxymethyl)-3-methoxyphenoxy]butyryl residue is a known linker, which is attached to a solid support having amino groups by forming an amide with the carboxyl of the butyric acid chain. N-Protected amino acids are attached to the hydroxyl of the 4-hydroxymethyl group via their carboxyl to form 2,4-dialkoxybenzyl esters, which can be readily cleaved in acid media when the synthesis is complete (Riniker et al., *Tetrahedron* 49, 9307–9312 (1993)). The drawback to such 2,4-dialkoxybenzyl esters is their instability with many of the reagents that are available for use in combinatorial synthesis resulting in cleavage of the ester.

A somewhat more stable ester is formed from 4-[4-(hydroxymethyl)phenoxy]butyric acid, described in European published application EP 445915. In this case, the ester was cleaved with a 90:5:5 mixture of trifluoroacetic acid, dimethyl sulfide and thioanisole.

When the desired product is a peptide amide, the 4-[4-(formyl)-3,5-dimethoxyphenoxy]butyryl residue has been employed as a linker. This particular linker is attached to a solid phase substrate via the carboxyl of the butyric acid chain, and the 4-formyl group is reductively aminated. N-Protected amino acids are then reacted with the alkylamine via their carboxyl to form 2,4,6-trialkoxybenzylamides. These may be cleaved by 1:1 trifluoroacetic acid in dichloromethane (PCT application WO97/23508).

If a photocleavable linker is used to attach chemical compounds to the main support, milder photolytic conditions of cleavage can be used which complement traditional acidic or basic cleavage techniques. A wider range of combinatorial synthetic conditions will be tolerated by photocleavable linkers (Gallop et al., *J. Med. Chem.* 37, 1233–1251 (1994); Gordon et al., *J. Med. Chem.* 37, 1385–1401 (1994)).

A phenacyl based linking group that is photocleavable has been described (Wang et al.,*J. Org. Chem.* 41, 3258 (1976)). The 4-bromomethyl-3-nitrobenzoyl residue has been widely employed as a photocleavable linker for both peptide acids and amides (Rich et al., *J. Am. Chem. Soc.* 97, 1575–1579 (1975); Hammer et al., Int.*J. Peptide Protein Res.* 36, 31–45 (1990)). This linker suffers from unduly slow cleavage rates, with typical photolysis times in organic solvents ranging from 12 to 24 hours. Moreover, photolytic cleavage of the linker generates a reactive and chromogenic nitrosoaldehyde on the resin support which can trap liberated compounds (Patchnornik et al., *J. Am. Chein. Soc.* 92, 6333–6335 (1970)). An α-methyl-2-nitrobenzyl linker was designed to obviate formation of the nitroso-aldehyde, but inefficient release of pentapeptides resulted due to swelling of the resin support (Ajajaghosh et al., *Tetrahedron* 44, 6661–6666 (1988)). Photocleavable linkers such as the 3-bromomethyl-4-nitro-6-methoxyphenoxyacetyl residue are stable to acidic or basic conditions yet, are rapidly cleavable under mild conditions and do not generate highly reactive byproducts (U.S. Pat. No. 5,739,386, issued Apr. 14, 1998).

It would be useful to have a linker-resin combination that would withstand a wider range of reaction conditions in combinatorial synthesis, but that could be readily and cleanly cleaved following completion of the solid phase synthesis.

SUMMARY OF THE INVENTION

The present invention relates to a linker-resin combination that demonstrates the ability to withstand many common reaction conditions and yet is cleavable under relatively mild conditions. In the following disclosure, the variables are defined when introduced and retain that definition throughout.

In one aspect, the invention relates to a substrate for solid phase synthesis comprising a solid phase-linker combination of the formula I:

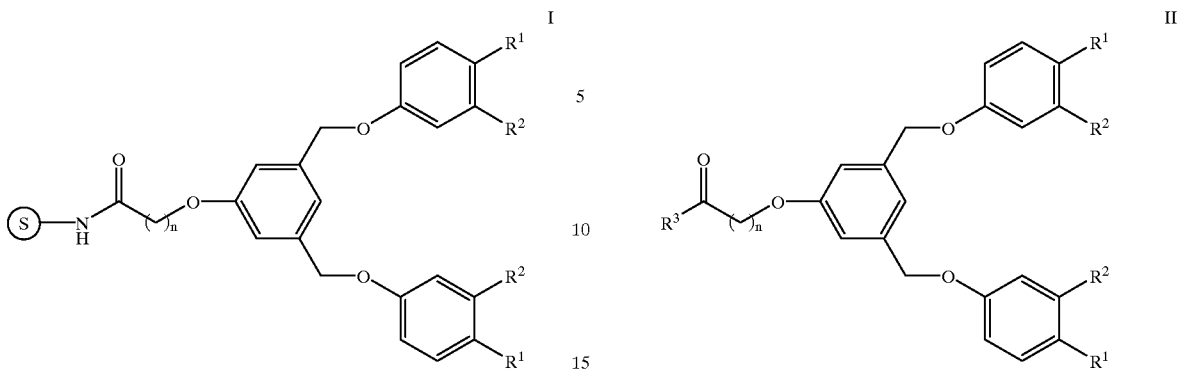

wherein:

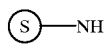

represents the residue of a solid support having a plurality of amino groups and the remainder constitutes the linker;
$R^1$ is —$NO_2$ or —CHO;
$R^2$ is —$OCH_3$, —CHO or —H; and
n=1 or 3.

Preferred solid phase supports are aminomethylated poly (styrene-co-divinylbenzene) and divinylbenzene-cross-linked resin, polyethyleneglycol-grafted polystyrene functionalized with amino groups.

In another aspect, the invention relates to a chemical intermediate of the formula II:

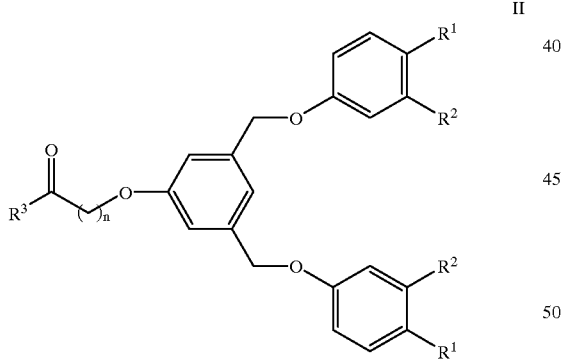

wherein:

$R^1$ is —$NO_2$ or —CHO;
$R^2$ is —$OCH_3$, —CHO or —H;
$R^3$ is chosen from the group consisting of hydroxyl, the residue of a solid support having a plurality of amino groups, and the residue of an ester; and n=1 or 3. A preferred ester residue is t-butoxy.

In a further aspect, the invention relates to processes for preparing the foregoing substrate for solid phase synthesis. One process comprises combining in a suitable solvent, a coupling agent, a solid support having a plurality of amino groups, and a compound of formula II:

wherein $R^3$ is hydroxyl. A preferred process is combining in a suitable solvent, a coupling agent, a solid support having a plurality of amino groups, and a compound of formula II wherein $R^1$ is —$NO_2$, $R^2$ is —CHO and $R^3$ is hydroxyl. In another preferred process, $R^1$ is —CHO and $R^2$ is —$OCH_3$. In yet another preferred process, $R^1$ is —CHO and $R^2$ is —H.

In yet another aspect, the invention relates to a process for solid phase synthesis comprising:

a) reacting a substrate for solid phase synthesis of the formula I:

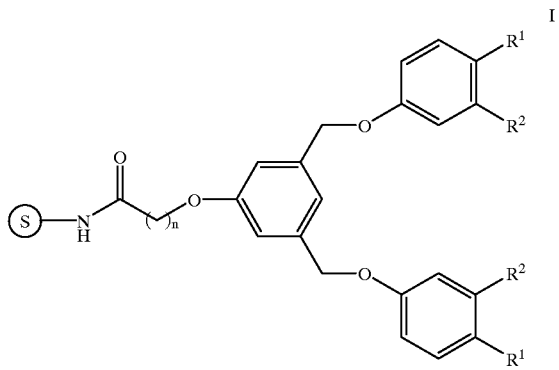

wherein:

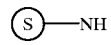

represents the residue of a solid support having a plurality of amino groups and the remainder constitutes the linker;
$R^1$ is —$NO_2$ or —CHO;
$R^2$ is —$OCH_3$, —CHO or —H; and
n=1 or 3,
with a reagent capable of reacting with an aldehyde to provide a support-linked synthon;

b) carrying out a plurality of chemical transformations on said support-linked synthon to provide a support-linked product; and c) treating said support-linked product with a condition of ultraviolet light or acid to cleave the product from the support and linker.

When $R^1$=—$NO_2$ and $R^2$=—CHO, the support-linked product is cleaved with ultraviolet light. When $R^1$=—CHO and $R^2$=—$OCH_3$, the support-linked product is cleaved by mild acid. When R¹=—CHO and R²=—H, the support-linked product is cleaved by a stronger concentration of acid. Trifluoroacetic acid is a preferred acid for cleavage.

In another aspect, the invention relates to a process for preparing a substrate for solid phase synthesis comprising:

combining in a suitable solvent, a coupling reagent, a solid support having a plurality of amino groups, a compound of the formula:

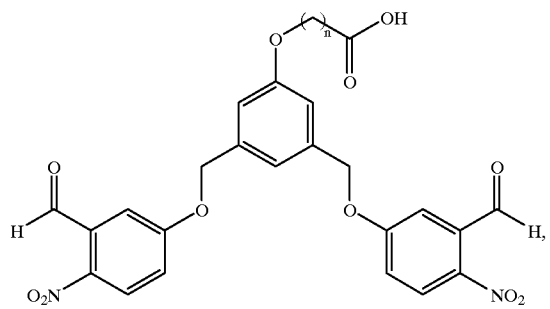

and a compound of the formula:

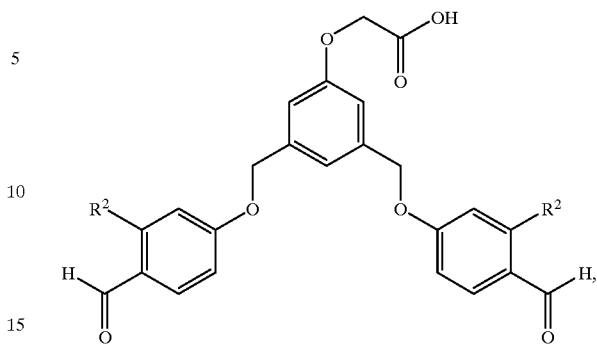

to produce said substrate of formula III:

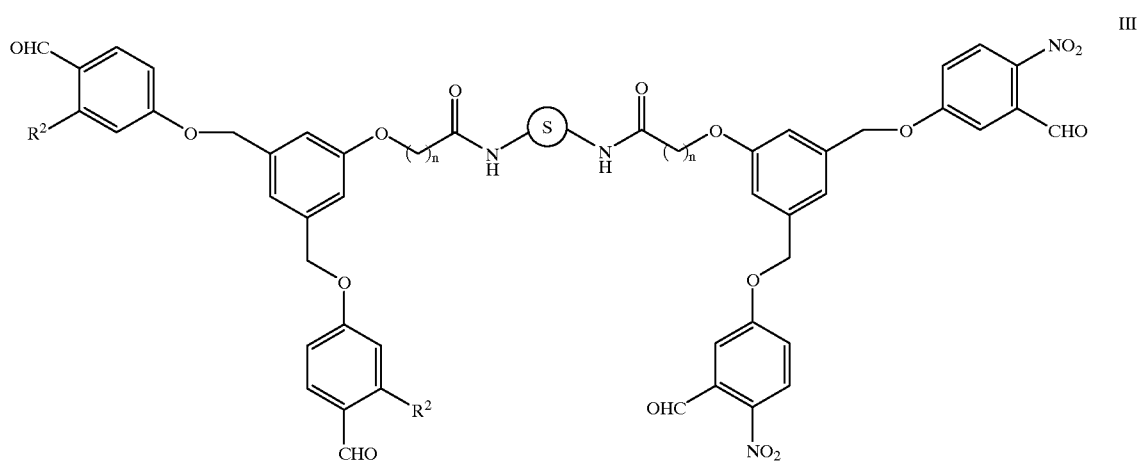

wherein:

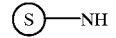

represents the residue of a solid support having a plurality of amino groups and the remainder constitutes the linker; R²=—OCH₃ or —H; and n=1 or 3.

In yet a further aspect, the invention relates to a process for solid phase synthesis comprising:

a) reacting a substrate for solid phase synthesis of the formula III:

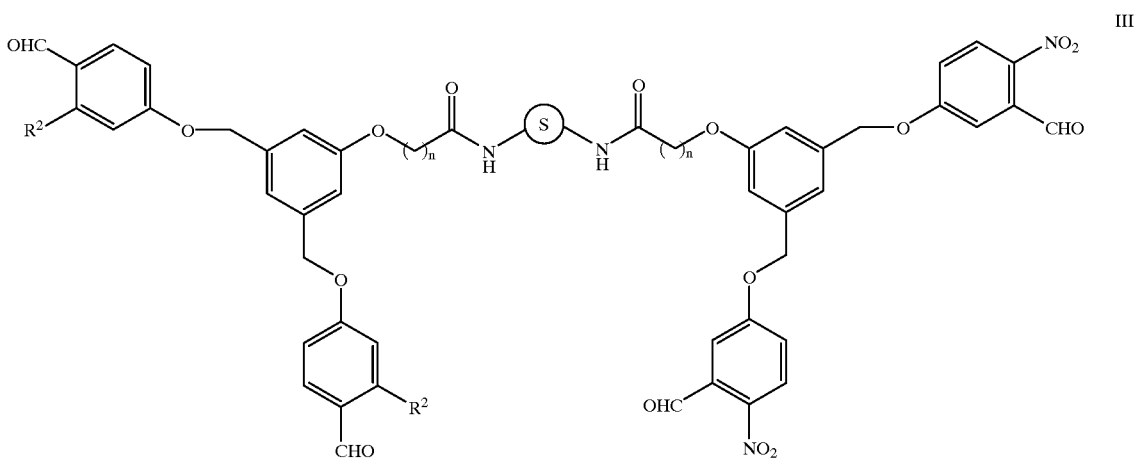

wherein:

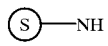

represents the residue of a solid support having a plurality of amino groups and the remainder constitutes a linker; $R^2$=—$OCH_3$ or —H; and n=1 or 3, with a reagent capable of reacting with an aldehyde to provide a support-linked synthon;

b) carrying out a plurality of chemical transformations on said support-linked synthon to provide a support-linked product;

c) treating said support-linked product with ultraviolet light to cleave the photocleavable support-linked product from the support and linker; and d) treating said support-linked product with trifluoroacetic acid to cleave the acid cleavable support-linked product from the support and linker.

When $R^2$=—$OCH_3$, trifluoroacetic acid (2–25%) in $CH_2Cl_2$ cleaves the support-linked product. When $R^2$=—H, trifluoroacetic acid (50–100%) in $CH_2Cl_2$ cleaves the support-linked product.

DETAILED DESCRIPTION OF THE INVENTION

Abbreviations and Definitions

The following abbreviations and terms have the indicated meanings throughout:
Ac=acetyl
$BH_3$=borane
BNB=4-bromomethyl-3-nitrobenzoic acid
Boc=t-butyloxy carbonyl
Bu=butyl
c-=cyclo-
$CH_2Cl_2$=dichloromethane=methylene chloride
DBU=diazabicyclo[5.4.0]undec-7-ene
DCM=dichloromethane=methylene chloride=$CH_2Cl_2$
DEAD=diethyl azodicarboxylate
DIC=diisopropylcarbodiimide
DIEA=N,N-diisopropylethyl amine
DMAP=4-N,N-dimethylaminopyridine
DMF=N,N-dimethylformamide
DMSO=dimethyl sulfoxide
DVB=1,4-divinylbenzene
EEDQ=2-ethoxy-1-ethoxycarbonyl- 1,2-dihydroquinoline
EtOAc=ethyl acetate
Fmoc=9-fluorenylmethoxycat-bonyl
GC=gas chromatography
h=hour
HATU=O-(7-Azabenzotriazol-1-yl)-1,1,3,3-tetramethyluronium hexafluorophosphate
HBr=hydrobromic acid=hydrogen bromide
HCl=hydrochloric acid=hydrogen chloride
HOAc=acetic acid
HOBt=hydroxybenzotriazole
in vacuo=under vacuum
L=liter
MCPBA=neta-chloroperbenzoic acid
Me=methyl
mesyl=methanesulfonyl
$MgSO_4$=magnesium sulfate
mL=milliliter
NaOH=sodium hydroxide
NMO=N-methylmorpholine oxide
PEG=polyethylene glycol
Ph=phenyl
PhOH=phenol
PfP=pentafluorophenol
PyBroP=bromo-tris-pyrrolidino-phosphonium hexafluorophosphate
rt=room temperature
sat'd=saturated
s-=secondary
sat.=saturated
t-=tertiary
TBDMS=t-butyldimethylsilyl
TFA=trifluoroacetic acid
THF=tetrahydrofuran
TLC=thin layer chromatography
TMOF=trimethyl orthoformate
TMS=trimethylsilyl
tosyl=p-toluenesulfonyl
Trt=triphenylmethyl "Alkyl" is intended to include linear or branched hydrocarbon structures and combinations thereof of 1 to 20 carbons. "Lower alkyl" means alkyl groups of from 1 to 6 carbon atoms. Examples of lower alkyl groups include methyl, ethyl, propyl, isopropyl, butyl, s-and t-butyl, pentyl, hexyl, and the like.

"Cycloalkyl" refers to saturated hydrocarbons of from 3 to 12 carbon atoms having one or more rings. Examples of "cycloalkyl" groups include c-propyl, c-butyl, c-pentyl, c-hexyl, 2-methylcyclopropyl, cyclopropylmethyl, cyclopentylmethyl, norbornyl, adamantyl, myrtanyl, and the like. "Lower cycloalkyl" refers to cycloalkyl of 3 to 6 carbons.

$C_1$ to $C_{20}$ hydrocarbon includes alkyl, cycloalkyl, alkenyl, alkynyl, aryl and combinations thereof. Examples include phenethyl, cyclohexylmethyl, and naphthylethyl.

"Alkoxy" means alkoxy groups of from 1 to 8 carbon atoms of a straight, branched, cyclic configuration and combinations thereof. Examples of alkoxy groups include methoxy, ethoxy, propoxy, isopropoxy, cyclopropyloxy, cyclohexyloxy, and the like. "Lower alkoxy" means alkoxy having 1–4 carbon atoms.

"Halo" means halogen. Examples include F, Cl, Br, and I.

"Fluoroalkyl" refers to an alkyl residue in which one or more hydrogen atoms are replaced with F, for example: trifluoromethyl, difluoromethyl, and pentafluoroethyl.

"Arylalkyl" denotes a residue comprising an alkyl attached to an aromatic or heteroaromatic ring. Examples include benzyl, phenethyl, 4-chlorobenzyl, and the like.

"Aryl" means an aromatic hydrocarbon radical of 4 to about 16 carbon atoms, preferably 6 to about 12 carbon atoms, more preferably 6 to about 10 carbon atoms. Examples of suitable aromatic hydrocarbon radicals include phenyl and naphthyl.

For the purpose of the present invention, the term "combinatorial library" means a collection of molecules based on logical design and involving the selective combination of building blocks by means of simultaneous chemical reactions. Each species of molecule in the library is referred to as a member of the library.

As will be understood by the person of skill in the art, the linkers of the invention could be used in combinatorial synthesis to attach tags as well as to attach the moiety of putative chemical or pharmacological interest. Tags are chemical entities which possess several properties: 1) they are detachable from the solid supports, preferably by means orthogonal to those employed for releasing the compound of pharmacological interest; 2) they are stable under the synthetic conditions; and 3) they are capable of being detected in very small quantities, e.g., $10^{-18}$ to $10^{-9}$ mole. Suitable tags and methods for their employment are described in Still et al., U.S. Pat. No. 5,565,324, the entire disclosure of which is incorporated herein by reference.

The materials upon which combinatorial syntheses are performed are referred to as solid supports, beads, and resins. These terms are intended to include: (a) beads, pellets, disks, fibers, gels, or particles such as cellulose beads, pore-glass beads, silica gels, polystyrene beads optionally cross-linked with divinylbenzene and optionally grafted with polyethylene glycol, poly-acrylamide beads, latex beads, dimethylacrylamide beads optionally cross-linked with N,N'-bis-acryloyl ethylene diamine, glass particles coated with hydrophobic polymer, etc., i.e., material having a rigid or semi-rigid surface; and (b) soluble supports such as polyethylene glycol or low molecular weight, non-cross-linked polystyrene. The solid supports may, and usually do, have functional groups such as amino, hydroxy, carboxy, or halo groups; where amino groups are the most common. Tentagel™ $NH_2$ (available from Rapp Polymere, Tubingen, Germany) is a preferred amine functionalized polyethylene glycol-grafted polystyrene resin. Techniques for functionalizing the surface of solid phases are well known in the art. Attachment of lysine to the amino groups on a bead (to increase the number of available sites) and subsequent attachment of linkers as well as further steps in a typical combinatorial synthesis are described, for example, in PCT application WO95/30642, the disclosure of which is incorporated herein by reference. In the synthesis described in WO95/30642, the linker is a photolytically cleavable linker, but the general principles of the use of a linker are well illustrated.

The invention relates to a substrate for solid phase synthesis comprising a solid phase-linker combination of the formula I:

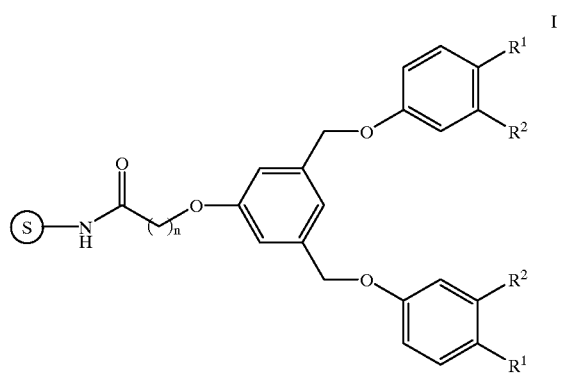

wherein:

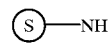

represents the residue of a solid support having a plurality of amino groups and the remainder constitutes the linker;

$R^1$ is —$NO_2$ or —CHO;

$R^2$ is —$OCH_3$, —CHO or —H; and n=1 or 3.

In these solid phase-linker combinations, the solid phase-linker combination is reacted with a reagent capable of reacting with an aldehyde to provide a support-linked synthon. A plurality of chemical transformations can be carried out on said supportlinked synthon to provide a support-linked product. This support-linked product is known as the combinatorial library member. When $R^1$ is $NO_2$ and $R^2$ is CHO, the support-linked product can be treated under conditions of ultraviolet light to cleave the product from the support and linker. When $R^1$ is CHO and $R^2$ is $OCH_3$, the support-linked product can be treated under conditions of mild acid to cleave the product from the support and linker. Usually trifluoroacetic acid (2–25%) in $CH_2Cl_2$ completes the cleavage. Likewise, when $R^1$ is CHO and $R^2$ is H, the support-linked product can be treated under acidic conditions to cleave the product from the support and linker. Cleavage conditions are usually trifluoroacetic acid (50–100%) in $CH_2Cl_2$.

Additionally, this invention relates to a substrate for solid phase synthesis comprising a solid phase-linker combination of the formula III:

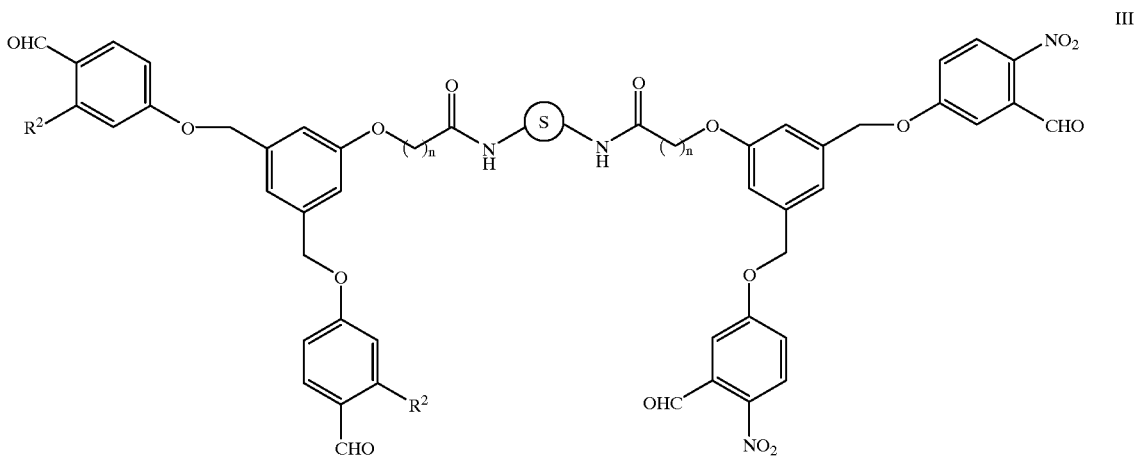

wherein:

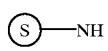

represents the residue of a solid support having a plurality of amino groups and the remainder constitutes the linker;

$R^2$ is $OCH_3$ or —H; and n=1 or 3.

In a process for solid phase synthesis, the solid phase-linker combination III is treated with a reagent capable of reacting with an aldehyde to provide a support-linked synthon. A plurality of chemical transformations can be carried out on said supportlinked synthon to provide a support-linked product. The support-linked product can be treated with ultraviolet light to cleave the photocleavable support-linked product from the support and linker. The cleaved product is then tested for biological activity. The remaining solid support-linked product is then treated with trifluoroacetic acid to cleave the acid cleavable support-linked product from the support and linker. When $R^2$=—$OCH_3$, milder acid conditions (2–25% $TFA/CH_2Cl_2$) are used to cleave the product. When $R^2$=—H, more concentrated acid (50–100% $TFA/CH_2Cl_2$) cleaves the product from the support. Again, the cleaved product is tested for biological activity. Cleaved products can also be tested for analytical properties (e.g., mass spectra, infrared, nuclear magnetic spectra, elemental analysis) and compound characteristics (e.g., solubility, stability, crystal structure) by methods known to those skilled in the art. In another mode, solid support-linked products can be tested for biological activity while on solid support and then cleaved at a later time. Typical examples of suitable biological assays are described in Baldwin et al., PCT application WO97/27315, the disclosure of which is incorporated herein by reference.

The solid phase-linker combinations were prepared by the following routes:

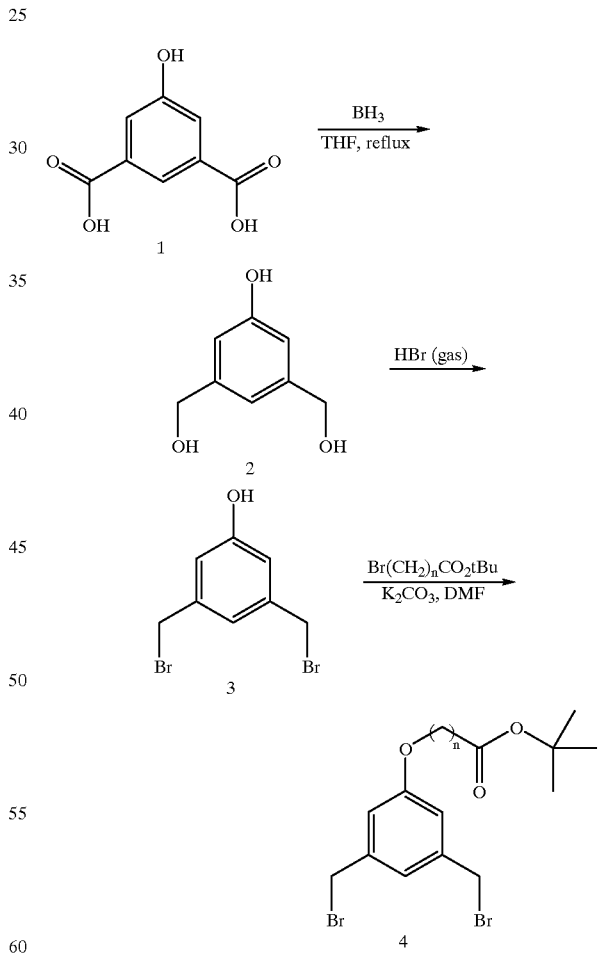

Commercially available, 5-hydroxyisophthalic acid 1 in THF was reduced with borane-THF to provide the triol 2. Treatment of the triol 2 with gaseous bromine afforded the dibromide 3. The dibromide 3 was treated with t-butyl bromoacetate (n=1) and potassium carbonate in DMF to provide the ester 4. As an alternative, t-butyl propionate (n=3) provided the ester 4 where n=3.

The photocleavable linker 5 and both the acid cleavable linkers, 6 and 7, were prepared from ester 4 as follows:

ality is completed by methods well known to those skilled in the art of the synthesis of combinatorial libraries on solid phase support. Coupling reagents include carbodiimides of various sorts, mixed anhydrides, EEDQ, HATU, and the

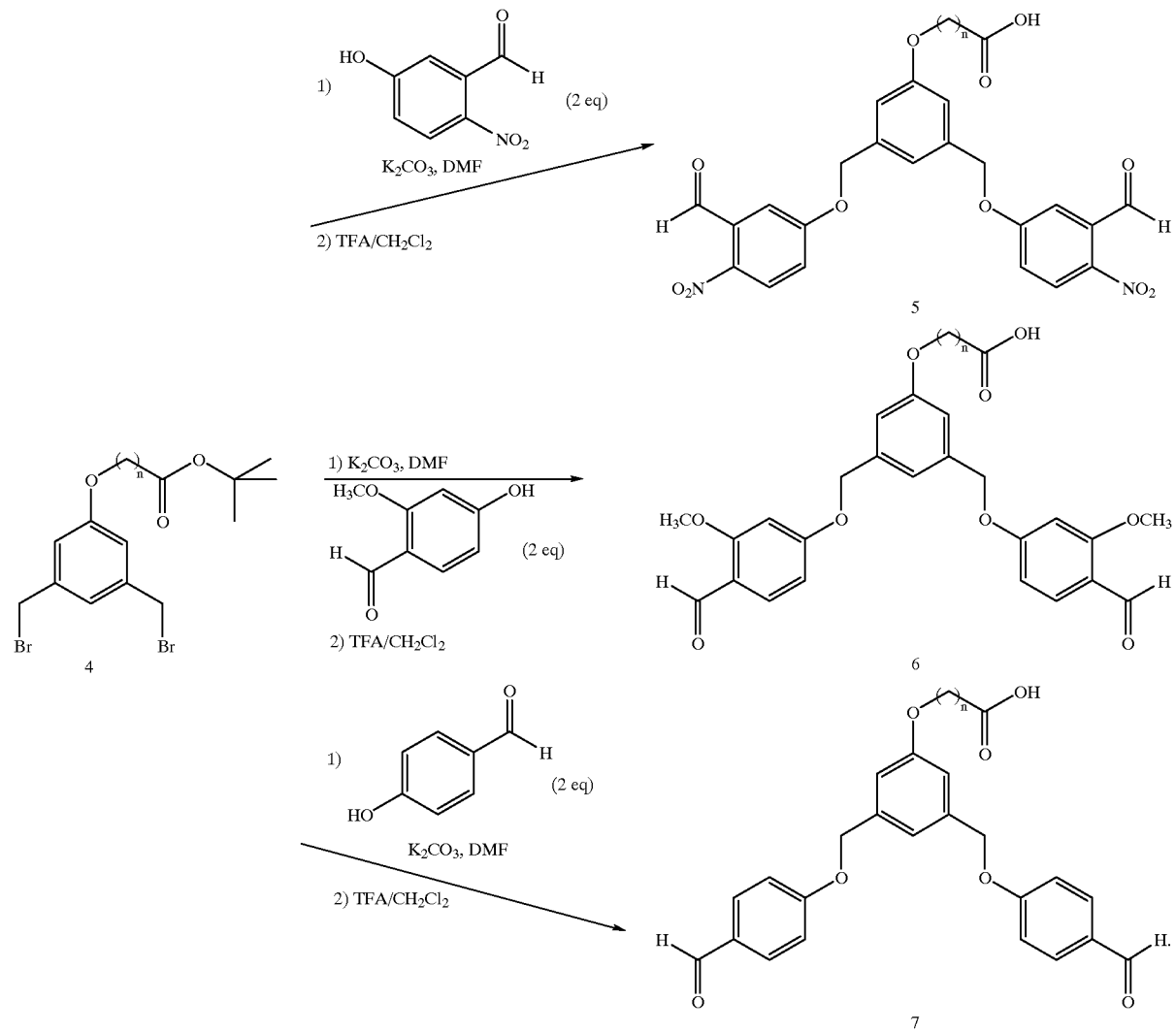

The ester 4 was treated with commercially available 5-hydroxy-2-nitrobenzaldehyde and potassium carbonate in DMF followed by treatment with 25% TFA in CH$_2$Cl$_2$ to afford the photocleavable linker 5. To afford the acid cleavable linker 6, ester 4 was treated with commercially available 4-hydroxy-2-methoxybenzaldehyde and potassium carbonate in DMF followed by treatment with 25% TFA in CH$_2$Cl$_2$. Treatment of ester 4 with 4-hydroxybenzaldehyde and potassium carbonate in DMF followed by 25% TFA in CH$_2$Cl$_2$ afforded the acid cleavable linker 7. These solid phase-linker combinations are "double loaded" on the di-(hydroxymethyl)phenoxy template which can be attached to the solid phase support. The ability to load increased amounts of compound on the "double load" solid phase-linker combinations is advantageous in solid phase combinatorial synthesis.

Condensation of the carboxylic acid portion of the linker with the solid phase support containing an amino functionlike. The carboxylic acid portion of the linker may be treated with leaving groups capable of forming "activated esters." Activated esters describe esters that are capable of undergoing a substitution reaction with primary or secondary amines to form an amide. Activated esters include esters "activated" by neighboring electron withdrawing substituents. Examples include esters of phenols, particularly electronegative substituted phenol esters such as pentafluorophenol esters; O-esters of isourea, such as arise from interaction with carbodiimides; O-esters of N-hydroxyimides and N-hydroxy heterocycles; specific examples include S-t-butyl esters, S-phenyl esters, S-2-pyridyl esters, N-hydroxypiperidine esters, N-hydroxysuccinimide esters, N-hydroxyphthalimide esters, and N-hydroxybenzotriazole esters. Solvents that are inert to the conditions of the condensation are "suitable solvents." These include, for example, THF, DMF, DCM, and the like.

Coupling of the photocleavable linker to the resin support to provide the photocleavable solid phase-linker combination is shown:

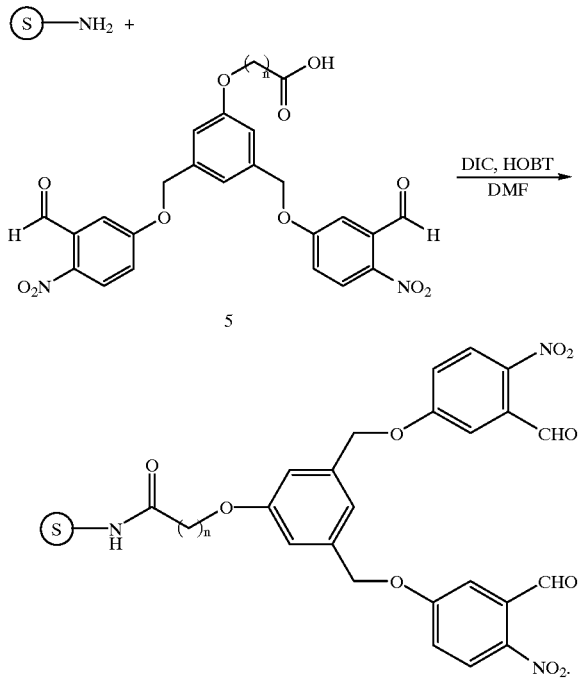

Coupling of the acid cleavable linker to the resin support to provide the acid cleavable solid phase-linker combination is shown:

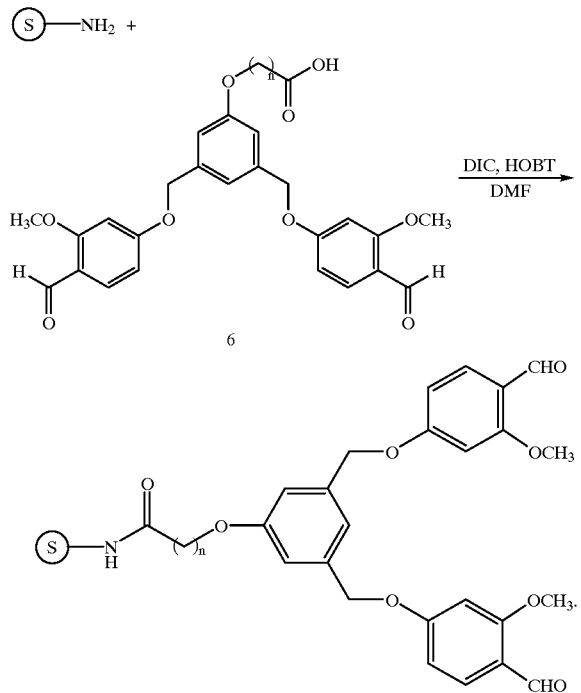

Coupling of the additional acid cleavable linker to the resin support to provide the more rigorous acid cleavable solid phase-linker combination is shown:

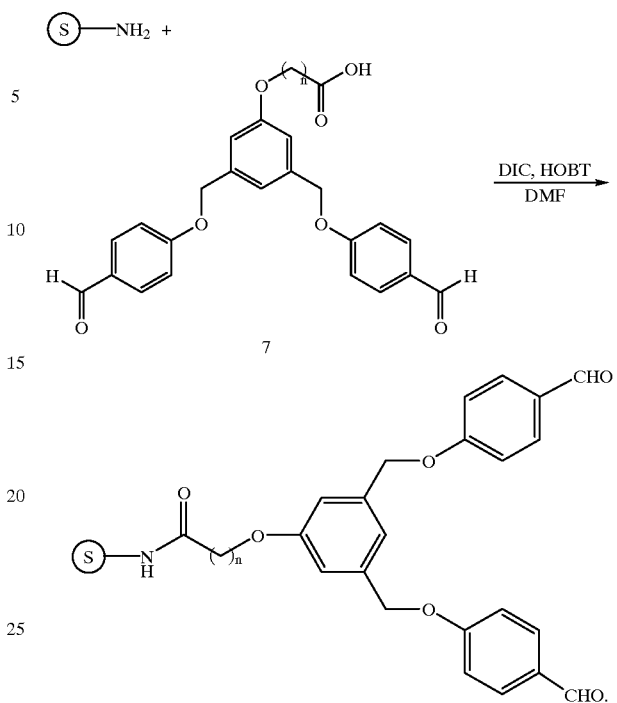

To improve the methods for making combinatorial libraries and the procedures for testing and analyzing the resulting library members, a solid phase-linker combination was synthesized which provided better control of the release of a support-linked product from the solid phase support. The dual solid phase-linker combination of formula III containing both the photocleavable solid phase-linker and the acid cleavable solid phase-linker allowed reliable cleavage of the support-linked products. A two stage, orthogonal release of a compound was achieved and based primarily upon the preloaded 1:1 ratio of the photocleavable/acid cleavable linker combinations. Photolytic cleavage permitted release of one half the total amount of support-linked product. Later, the remaining product was cleaved reliably under acid conditions in good overall yield. The advantage of employing such dual solid phase-linker combinations over the current linker technology is that this system reliably achieved the release of the product over a two-stage sequence in approximately 1:1 ratio. The orthogonal cleavage mechanisms of this dual solid phase-linker combination avoided the unnecessary development of a complicated kinetic cleavage profile.

A dual solid phase-linker combination of formula III ($R^2$=—$OCH_3$) was prepared by coupling a 1:1 mixture of the photocleavable linker 5 and the acid cleavable linker 6 with the chosen aminomethylated resin support under known conditions. Later, a two-stage cleavage of attached compounds was achieved using photolysis followed by mild acid conditions.

To develop a solid phase-linker combination that provides a linker with greater stability under more acidic synthetic conditions, a dual solid phase-linker combination of formula III ($R^2$=—H) was prepared by coupling a 1:1 mixture of the photocleavable linker 5 and the acid cleavable linker 7 with the chosen aminomethylated resin support under known conditions. Demonstrated release of attached compounds from the dual solid phase-linker combination was provided by photolysis and then treatment with acid conditions.

vessel was capped and the resulting light brown solution continued to stir at room temperature until complete disappearance of triol 2 (TLC). The solvent was removed and the

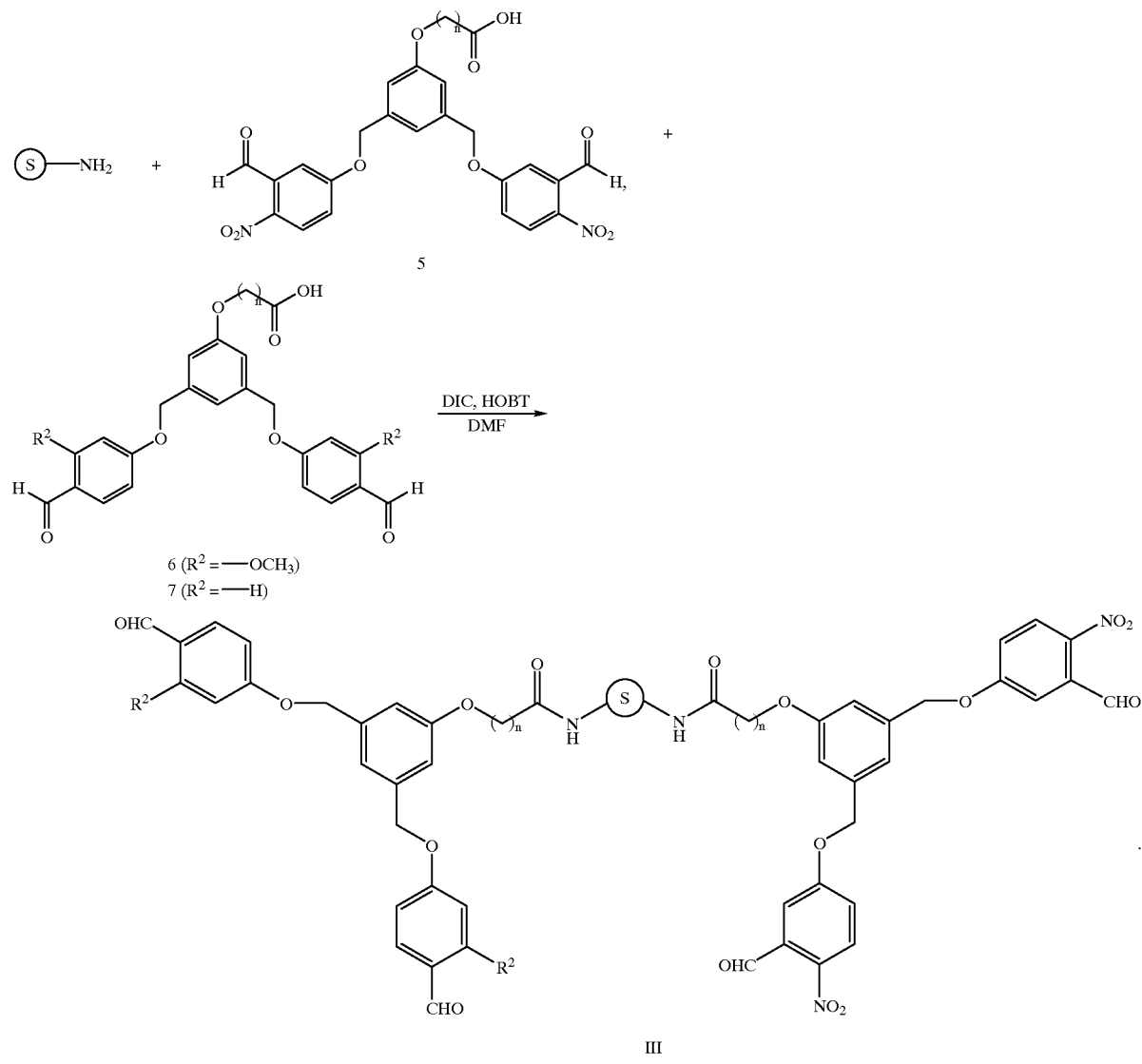

Methods of Synthesis 3,5-di-(hydroxymethyl)phenol (2)

To a solution of 5-hydroxyisophthalic acid 1 (30 g, 0.17 mol) in THF (1 L) at room temperature was added slowly a solution of $BH_3$ (800 mL, 1 M in THF). The resulting heterogeneous mixture was warmed to reflux overnight. The reaction mixture was cooled to room temperature whereupon 0.8 L of 1M HCl was carefully added. The resulting homogenous solution was concentrated in vacuo and the residues were treated with NaOH (42 g, 1.05 mol). Water was removed from the solution via concentration in vacuo and the residues were extracted with EtOAc (3×350 mL). The combined organic layers were dried ($MgSO_4$), filtered and concentrated in vacuo to give 28 g (93%) of triol 2 as thick colorless oil.

3,5-di-(bromomethyl)phenol (3)

Triol 2 (55 g, 0.37 mmol) in chloroform (500 mL) at room temperature was bubbled with HBr gas for 2 h. The reaction residues were washed with sat. aqueous $NaHCO_3$. The aqueous layer was extracted with EtOAc (3×150 mL) and the combined organic layers were dried ($MgSO_4$), filtered and concentrated in vacuo to provide 83.4 g (91% based on acid 1) of dibromide 3 as a light brown solid.

t-butyl 3,5-di-(bromomethyl)phenoxyacetate (4, n=1)

Dibromide 3 (30 g, 0.11 mol) in DMF (750 mL) at room temperature was treated with potassium carbonate (45 g, 0.32 mol) and t-butyl bromoacetate (48 ml, 0.32 mol) was added dropwise to the solution. The resulting mixture was stirred at room temperature for overnight. Water (300 mL) and EtOAc (500 mL) were added and the layers were separated. The aqueous layer was extracted with EtOAc (3×100 mL) and the combined organic layers were dried ($MgSO_4$), filtered and concentrated in vacuo to afford ester 4 which was purified on silica gel (30:1-hexane:EtOAc). Further purification was accomplished by recrystallization with a mixture of hexane and diethyl ether (10:1) to give the ester4 as white solid.

Photocleavable Linker (5)

The mixture of ester 4 (9.5 g, 24 mmol), potassium carbonate(13.3 g, 96.4 mmol) and 5-hydroxy-2-nitrobenzaldehyde (8.1 g, 48.2 mmol) in DMF (250 mL) was stirred at room temperature for 18 h. Water (200 mL) and EtOAc (200 mL) were added and the layers were separated. The aqueous layer was extracted with EtOAc (3×100 mL) and the combined organic layers were dried ($MgSO_4$), filtered and concentrated in vacuo. The residues were treated with 25% TFA in $CH_2Cl_2$ (150 mL) and stirred at room temperature for 2 h. Alter removing the solvent, the residues were washed with $Et_2O$ (2×50 mL) and the resulting acid 5 was dried in vacuo to afford yellow solids.

Acid Cleavable Linker (6)

The mixture of ester 4 (3.0 g, 7.6 mmol), potassium carbonate (4.2 g, 30 mmol) and 4-hydroxy-2-methoxybenzaldehyde (2.3 g, 15 mmol) in DMF (75 mL) was stirred at room temperature for 18 h. Water (100 mL) and EtOAc (100 mL) were added and the layers were separated. The aqueous layer was extracted with EtOAc (3×50 mL) and the combined organic layers were dried ($MgSO_4$), filtered and concentrated in vacuo. The residues were treated with 25% TFA in $CH_2Cl_2$ (100 mL) and stirred at room temperature for 2 h. After removing the solvent, the residues were washed with $Et_2O$ (2×50 mL) and dried in vacuo to provide the resulting acid 6 as white solids.

Acid Cleavable Linker (7)

The mixture of ester 4 (3.0 g, 7.6 mmol), potassium carbonate (4.2 g, 30 mmol) and 4-hydroxybenzaldehyde (1.8 g, 15 mmol) in DMF (75 mL) was stirred at room temperature for 18 h. Water (100 mL) and EtOAc (100 mL) were added and the layers were separated. The aqueous layer is extracted with EtOAc (3×50 mL) and the combined organic layers were dried ($MgSO_4$), filtered and concentrated in vacuo. The residues were treated with 25% TFA in $CH_2Cl_2$ (100 mL) and stirred at room temperature for 2 h. After removing the solvent, the residues were washed with $Et_2O$ (2×50 mL) and dried in vacuo to afford the acid 7 as white solids.

Attachment of Linker to Resin:

Photocleavable Solid Phase-Linker (5) Combination

TentaGel™ resin (S—$NH_2$, 10 g, 0.3 mmol/g, 3.0 mmol, 180–220 μm) was suspended in a solution of acid 5 (3.1 g, 6.0 mmol) and HOBT (0.81 g, 6.0 mmol) in DMF (35 mL), then treated with DIC (1.9 mL, 12 mmol). The suspension was shaken for 15 h, then the resin was washed with DMF (3×5(mL) and $CH_2Cl_2$ (3×50 mL).

Acid Cleavable Solid Phase-Linker (6) Combination

TentaGel™ resin (S—$NH_2$, 10.0 g, 0.33 mmol/g, 3.3 mmol, 180–220 μm) was suspended in a solution of acid 6 (3.2 g, 6.6 mmol) and HOBT (0.89 g, 6.6 mmol) in DMF (40 mL), then treated with DIC (2.1 mL, 13.2 mmol). The suspension was shaken for 15 h, then the resin was washed with DMF (3×50 mL) and $CH_2Cl_2$ (3×50 mL).

Acid Cleavable Solid Phase-Linker (7) Combination

TentaGe™ resin (S—$NH_2$, 10.0 g, 0.33 mmol/g, 3.3 mmol, 180–220 μm) was suspended in a solution of acid 7 (2.8 g, 6.6 mmol) and HOBT (0.89 g, 6.6 mmol) in DMF (40 mL), then treated with DIC (2.1 mL, 13.2 mmol). The suspension was shaken for 15 h, then the resin was washed with DMF (3×50 mL) and $CH_2Cl_2$ (3×50 mL).

Attachment of 1:1/Photocleavable Linker (5): Acid Cleavable Linker (6) to Resin (III)

TentaGe™ resin (S—$NH_2$, 630 mg, 0.33 mmol/g, 0.21 mmol, 180–220 μm) was suspended in a solution of acid 5 (106 mg, 0.21 mmol), acid 6 (100 mg, 0.21 mmol) and HOBT (56 mg, 0.42 mmol) in DMF (6 mL), then treated with DIC (129 μL, 0.83 mmol). The suspension was shaken for 15 h, then the resin was washed with DMF (3×20 mL) and $CH_2Cl_2$ (3×20 mL).

Attachment of 1:1/Photocleavable Linker (5): Acid Cleavable Linker (7) to Resin (III) TentaGe™ resin (S—$NH_2$, 630 mg, 0.33 mmol/g, 0.21 mmol, 180–220 μm) was suspended in a solution of acid 5 (106 mg, 0.21 mmol), acid 7 (88 mg, 0.21 mmol) and HOBT (56 mg, 0.42 mmol) in DMF (6 mL), then treated with DIC (129 μL, 0.83 mmol). The suspension was shaken for 15 h, then the resin was washed with DMF (3×20 mL) and $CH_2Cl_2$ (3×20 mL).

For combinatorial synthesis, either the photocleavable or acid cleavable solid phase-linker combination (formula I) or the dual solid phase-linker combination (formula III) is reacted with a primary or secondary amine or any compound known to react with an aldehyde. The choice of reagent is immaterial to the present invention and is determined by the nature of the combinatorial library sought to be synthesized. The number and nature of further reactions of the support-linked synthon is similarly dictated by the needs of the library. When the combinatorial synthesis is complete, the photocleavable linker is cleaved from the resin by photolysis in methanol. When the combinatorial synthesis is completed using an acid cleavable linker, the linker is cleaved from the resin by treatment with acid, preferably trifluoroacetic acid in dichloromethane, or HCl in diethyl ether or dioxane. When the combinatorial library is synthesized upon the dual solid phase-linker combination, the library product can be cleaved in approximately 50% yield with ultraviolet light. Complete cleavage of the remaining product is carried out under appropriate acidic conditions.

The above discussion of this invention is directed primarily to the preferred embodiments and practices thereof. It will be understood to those skilled in the art that further changes and modifications in the actual implementation of the teachings described herein could be made without departing from the spirit and the scope of the invention as defined in the following claims.

We claim:

1. A process for solid phase synthesis comprising:

a) reacting a substrate for solid phase synthesis of the formula I:

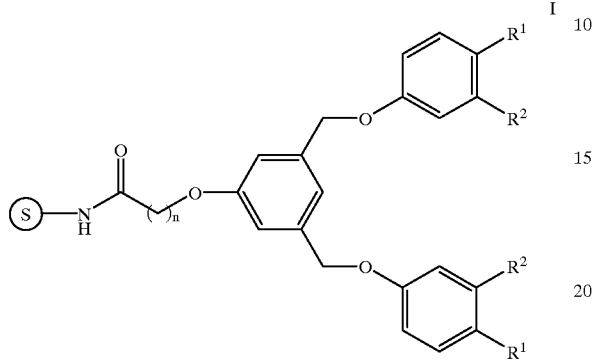

wherein:

represents a solid support having a plurality of amino groups;

$R^1$ is —$NO_2$;

$R^2$ is —CHO; and n=1 or 3, with an amine under conditions for reductive amination to provide a support-linked amine;

b) carrying out a plurality of chemical transformations on said support-linked amine to provide a support-linked product; and c) exposing said support-linked product to ultraviolet light to cleave the product from the support and linker.

2. A process for solid phase synthesis comprising:

a) reacting a substrate for solid phase synthesis of the formula I:

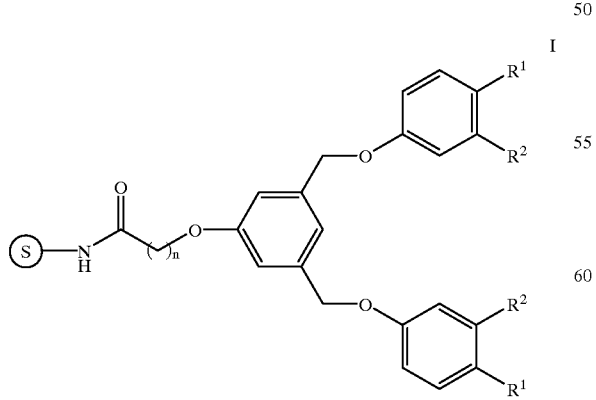

wherein:

represents a solid support having a plurality of amino groups;

$R^1$ is —CHO;

$R^2$ is —$OCH_3$; and n=1 or 3, with an amine under conditions for reductive amination to provide a support-linked amine;

b) carrying out a plurality of chemical transformations on said support-linked amine to provide a support-linked product; and c) reacting said support-linked product with acid to cleave the product from the support and linker.

3. A process for solid phase synthesis comprising:

a) reacting a substrate for solid phase synthesis of the formula I:

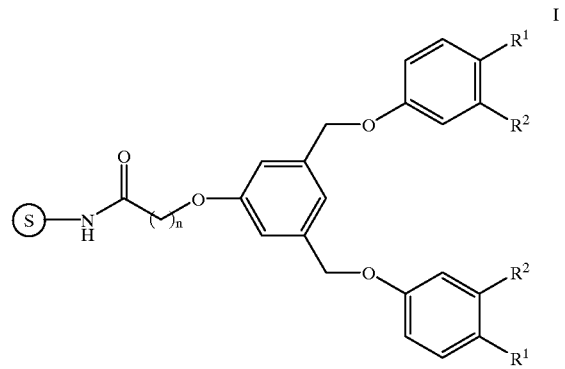

wherein:

represents a solid support having a plurality of amino groups;

$R^1$ is —CHO;

$R^2$ is —H; and n=1 or 3, with an amine under conditions for reductive amination to provide a support-linked amine;

b) carrying out a plurality of chemical transformations on said support-linked amine to provide a support-linked product; and c) reacting said support-linked product with an acid to cleave the product from the support and linker.

4. A process for solid phase synthesis comprising:

a) reacting a substrate for solid phase synthesis of the formula III:

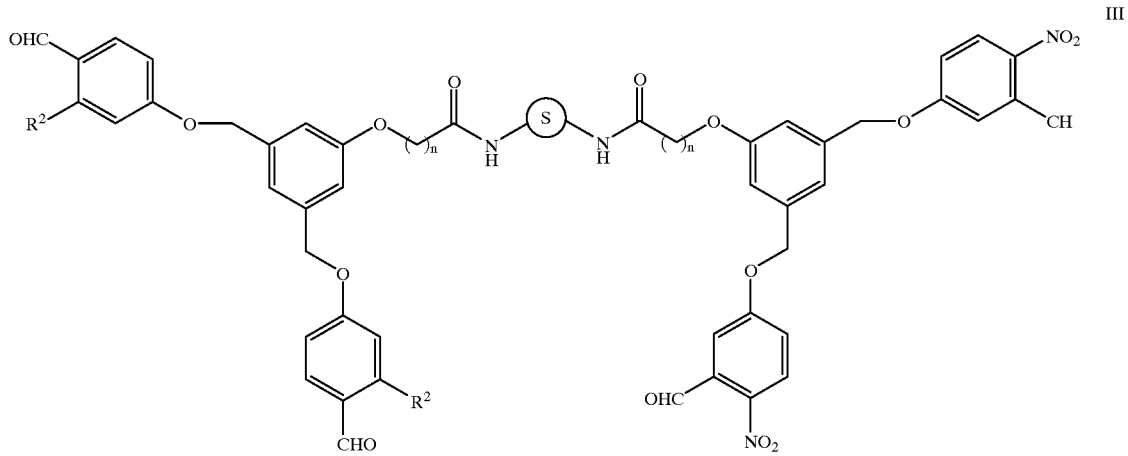

wherein:

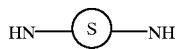

represents a solid support having a plurality of amino groups;

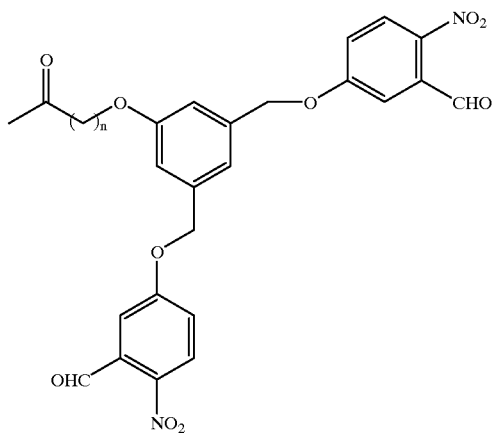

represents a first linker,

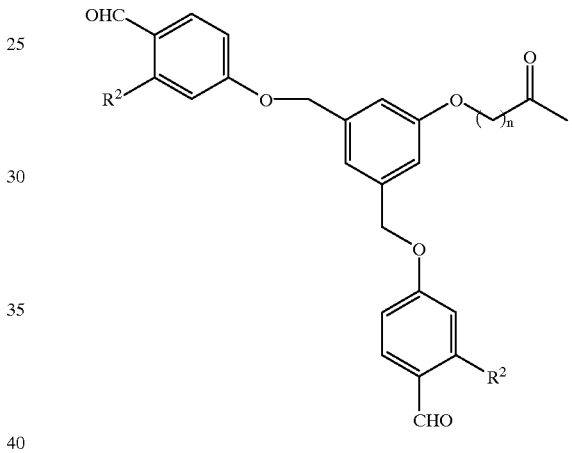

represents a second linker in which $R^2$=—$OCH_3$, and n=1 or 3, with an amine under conditions for reductive amination to provide a support-linked amine;

b) carrying out a plurality of chemical transformations on said support-linked amine to provide a support-linked product;

c) exposing said support-linked product to ultraviolet light to cleave the product from the support and said first linker; and d) reacting said support-linked product with trifluoroacetic acid to cleave the support-linked product from the support and said second linker.

5. A process for solid phase synthesis comprising:

a) reacting a substrate for solid phase synthesis of the formula III:

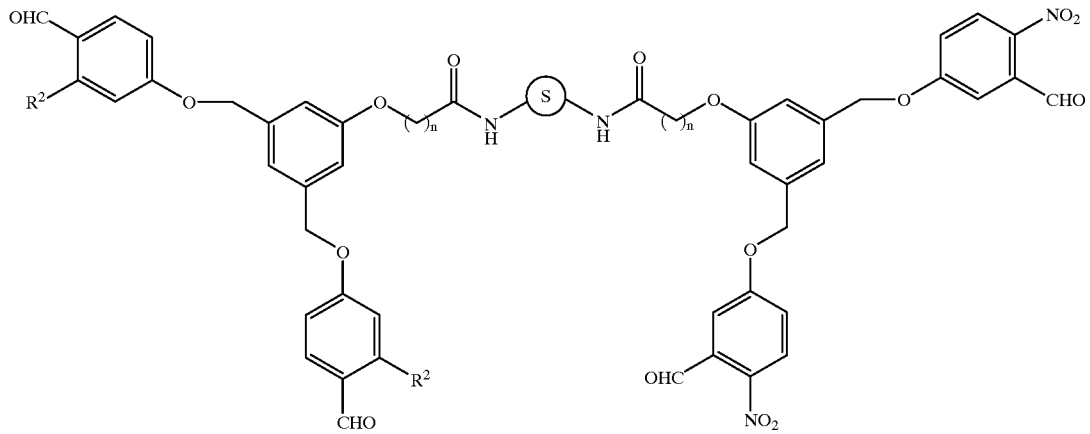

wherein:

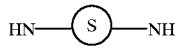

represents a solid support having a plurality of amino groups;

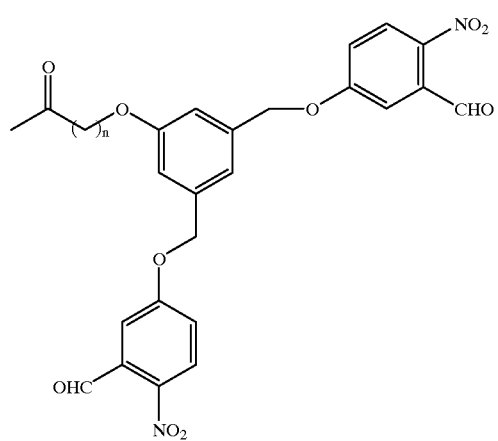

represents a first linker,

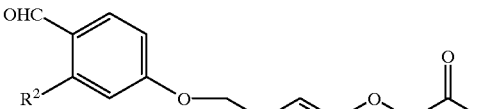

represents a second linker in which $R^2$=—H, and n=1 or 3,
    with an amine under conditions for reductive amination to provide a support-linked amine;
b) carrying out a plurality of chemical transformations on said support-linked amine to provide a support-linked product;
c) exposing said support-linked product to ultraviolet light to cleave the product from the support and said first linker; and
d) reacting said support-linked product with trifluoroacetic acid to cleave the support-linked product from the support and said second linker.

* * * * *